United States Patent [19]

Eidenschink et al.

[11] Patent Number: 4,868,341

[45] Date of Patent: Sep. 19, 1989

[54] BICYCLOHEXYLS

[75] Inventors: Rudolf Eidenschink, Münster; Michael Römer, Rodgau; Georg Weber, Erzhausen, all of Fed. Rep. of Germany; George W. Gray, North Humberside; Kenneth J. Toyne, Hull, both of Great Britain

[73] Assignees: Merck Patent Gesellschaft Mit Beschrankter Haftung, Darmstadt, Fed. Rep. of Germany; The Secretary of State for Defence in Her Majesty's Government of the United Kingdom of Great Britain and Northern Ireland, London, England

[21] Appl. No.: 907,262

[22] Filed: Sep. 15, 1986

Related U.S. Application Data

[63] Continuation-in-part of Ser. No. 620,775, Jun. 14, 1984, Pat. No. 4,622,164.

[30] Foreign Application Priority Data

Jun. 14, 1983 [DE] Fed. Rep. of Germany ....... 3321373

[51] Int. Cl.$^4$ ............................................. C07C 43/184
[52] U.S. Cl. .................................................... 568/664
[58] Field of Search ......................................... 568/664

[56] References Cited

U.S. PATENT DOCUMENTS

| | | | |
|---|---|---|---|
| 4,198,130 | 4/1980 | Boller et al. | 350/350 |
| 4,331,552 | 5/1982 | Eidenschink et al. | 585/20 |
| 4,398,803 | 8/1983 | Pohl et al. | 350/334 |
| 4,507,222 | 3/1985 | Inoue et al. | 568/664 |
| 4,622,164 | 11/1986 | Eidenschink et al. | 568/606 X |

FOREIGN PATENT DOCUMENTS 0058981 9/1982 European Pat. Off. .
2080561 2/1982 United Kingdom .

OTHER PUBLICATIONS

H. Kelker/R. Hatz, Handbook of Liquid Crystals, Verlag Chemie, Weinheim, 1980, pp. 34–37.
Demus, Mitteilungblatt der Cemischen Gesellschaft der DDR, 28, 1981, pp. 145–151.
Gray, Mol. Cryst. Liq. Cryst. 1981, vol. 63, pp. 3–17.
Eidenschink, Chemie in Unserer Zeit, vol. 18, No. 5, 1984.

Primary Examiner—John W. Rollins
Assistant Examiner—W. Catchpole
Attorney, Agent, or Firm—Millen, White & Zelano

[57] ABSTRACT

New bicyclohexyls of the formula I $$R^1-Cy-Cy-R^2$$

wherein $R^1$ and $R^2$ are each alkyl which has 1–10 C atoms and in which one or two $CH_2$ group(s) can be replaced by 0 atoms, and Cy is 1,4-cyclohexylene, are suitable for use as the coponents of liquid-crystal dielectrics.

9 Claims, No Drawings

BICYCLOHEXYLS

This application is a continuation-in-part of application Ser. No. 620,775, filed June 14, 1984 now U.S. Pat. No. 4,622,164.

SUMMARY OF THE INVENTION

It is an object of this invention to provide new stable liquid-crystal or mesogenic compounds which are suitable as components of liquid-crystal dielectrics.

Upon further study of the specification and appended claims, further objects and advantages of this invention will become apparent to those skilled in the art.

These objects have been achieved by the provision of new bicyclohexyls of the formula I $$R^1-Cy-Cy-R^2$$

wherein $R^1$ and $R^2$ are each alkyl which has 1–10 C atoms and in which one or two non-adjacent $CH_2$ group(s) can be replaced by 0 atoms, and Cy is 1,4-cyclohexylene.

DETAILED DISCUSSION

Like similar compounds, for example those known from German Offenlegungsschrift 2,702,598, these substances can be used as components of liquid-crystal dielectrics, in particular for displays which are based on the principle of the twisted cell, the guest-host effect of the deformation of aligned phases or the effect of dynamic scattering.

It has been found that the bicyclohexyls of the formula I are excellently suitable for use as components of liquid-crystal dielectrics. In particular, it is possible with their aid to produce stable liquid-crystal phases having a relatively low optical anisotropy and having a high nematic character which, in electrooptical display elements based on the principle of the twisted cell and/or the guest-host principle, are distinguished by a particularly advantageous angular dependence of the contrast.

In addition, the provision of the compounds of the formula I broadens considerably, in a very general manner, the range of liquid-crystal substances which are suitable from a variety of technical aspects relating to their use for the production of nematic mixtures.

The compounds of the formula I have a wide range of application. Depending on the choice of the ubstituents, these compounds can be used as the base materials of which liquid-crystal dielectrics are predominantly composed; it is also possible, however, to add compounds of the formula I to liquid-crystal base materials belonging to other classes of compounds, in order to exert an influence on the optical anistropy or the angular dependence of the contrast of such a dielectric.

In the pure state, the compounds of the formula I are colorless and form liquid-crystal mesophases within a temperature range which is advantageously situated for electrooptical use. They are very resistant to chemicals, heat and light.

The invention relates, therefore, to the bicyclohexyls of the formula I and to a process for their preparation which comprises treating with a reducing agent a compound which in other respects corresponds to the formula I, but contains one or more reducible group(s) and/or C—C bond(s) instead of H atoms, or etherifying a corresponding alcohol in order to prepare ethers of the formula I (wherein at least one of the radicals $R^1$ and $R^2$ is an alkyl group wherein one or two $CH_2$ group(s) have been replaced by 0 atoms). The invention also relates to the use of the compounds of the formula I as components of liquid-crystal dielectrics. The invention also relates to liquid-crystal dielectrics containing at least one compound of the formula I and to electrooptical display elements containing dielectrics of this type.

In the preceding and following text, unless anything contrary is expressly recorded, the radicals $R^1$, $R^2$ and Cy have the meanings indicated.

In the compounds of the formula I, preferred stereoisomers are those wherein the two 1,4-substituents are in each case in the trans-position relative to one another.

The radicals $R^1$ and $R^2$ are preferably alkyl having 1–10, in particular 3, 4, 5, 6, 7 or 8, C atoms, and also alkoxy or alkoxymethyl each of which has up to 10, preferably 2, 3, 4, 5, 6, 7 or 8, C atoms. They are preferably linear and are therefore preferably propyl, butyl, pentyl, hexyl, heptyl and octyl and also ethoxy, propoxy, butoxy, pentoxy, heptoxy, octoxy, methoxymethyl, ethoxymethyl, propoxymethyl, butoxymethyl, pentoxymethyl, hexoxymethyl and heptoxymethyl, and also methyl, ethyl, nonyl, decyl, methoxy, nonoxy, decoxy, octoxymethyl, nonoxymethyl and other linear oxaalkyl and dioxaalkyl groups, such as 3-oxabutyl (=2-methoxyethyl), 3-oxapentyl, 4-oxapentyl, 3-, 4- or 5-oxahexyl, 3-, 4-, 5- or 6-oxaheptyl, 3-, 4-, 5-, 6- or 7-oxaoctyl, 3-, 4-, 5-, 6-, 7- or 8-oxanonyl, 2-, 3-, 4-, 5-, 6-, 7-, 8- or 9-oxadecyl, 1,3-dioxabutyl (=methoxymethoxy), 1,3-, 1,4- or 2,4-dioxapentyl or 1,3-, 1,4-, 1,5-, 2,4-, 2,5- or 3,5-dioxahexyl.

Compounds of the formula I having branched wing groups $R^1$ and/or $R^2$ can occasionally be of importance owing to improved solubility in the customary liquid-crystal base materials, but can, in particular, be of importance as chiral doping substances if they are optically active. As a rule, branched groups $R^1$ or $R^2$ do not contain more than one chain branching.

Branched radicals $R^1$ or $R^2$ which are preferred are isopropyl, 1-methylpropyl (sec.-butyl) or 2-methylpropyl (isobutyl), 2-methylbutyl, 3-methylbutyl (isopentyl), 2-methylpentyl, 3-methylpentyl, 1-methylhexyl, 2-ethylhexyl, 2-propylpentyl, 1-methylheptyl, isopropoxy, 2-methylpropoxy, 2-methylbutoxy, 3-methylbutoxy, 2-methylpentoxy, 3-methylpentoxy, 2-ethylhexoxy, 1-methylhexoxy, 1-methylheptoxy, 2-oxa-3-methylbutyl or 3-oxa-4-methylpentyl.

Among the compounds of the formula I, preferred compounds are those in which at least one of the radicals $R^1$ and $R^2$ has one of the preferred meanings indicated. Particularly preferred groups of compounds correspond to the formula Ia and Ib:

Alkyl—Cy—Cy—alkyl            Ia

Alkyl—Cy—Cy—alkoxy           Ib wherein the alkyl and alkoxy groups have 1–10, preferably 2–8, C atoms and are preferably linear, and the two alkyl groups in Ia can be identical or different from one another.

The compounds of the formula I are prepared by methods which are in themselves known, such as are described in the literature (for example in the standard works such as Houben-Weyl, Methoden der Organischen Chemie ("Methods of Organic Chemistry"), Georg-Thieme-Verlag, Stuttgart), namely under reaction conditions which are known and suitable for the reactions mentioned. In this respect it is also possible to make use of variants which are in themselves known but are not mentioned here in detail.

If desired, the starting materials can also be formed in situ in a procedure in which they are not isolated from the reaction mixture, but are immediately reacted further to give the compounds of the formula I.

Suitable reducible groups are preferably carbonyl groups, in particular keto groups and also, for example, aldehyde groups or free or esterified hydroxyl groups. Preferred starting materials for the reduction correspond to the formula I, but contain a cyclohexene or benzene ring instead of a cyclohexane ring and/or contain a —CO— group instead of a —CH$_2$— group and/or contain a free or functionally modified OH group (for example an OH group in the form of its p-toluenesulfonate) instead of an H atom.

These starting materials are either known or can be prepared in a manner which is in itself known. Thus phenylcyclohexanes of the type R$^1$—Cy—Phe—R$^2$ (wherein Phe is a 1,4-phenylene group) are known from German Offenlegungsschrift 2,636,684. Cyano bicyclohexyls of the type R$^1$—Cy—Cy—CN are known from German Offenlegungsschrift 2,702,598. From these it is possible to prepare, by Grignard reactions, ketones of the type R$^1$—Cy—Cy—CO—R$^3$ wherein R$^3$ is alkyl which has 1–9 C atoms and in which one or two CH$_2$ group(s) can also be replaced by O atoms. Hydrolysis of the cyano bicyclohexyls gives carboxylic acids of the formula R$^1$—Cy—Cy—COOH, which can be reduced to give carbinols of the formula R$^1$—Cy—Cy—CH$_2$OH. Carbinols of the formula R$^1$—Cy—Cy—CHOH—R$^3$ can be obtained by reducing the abovementioned ketones. Reacting 4-R$^1$-cyclohexanones with Grignard compounds of the formula R$^2$—Cy—MgBr gives, after hydrolysis, 1-(4-R$^2$-Cy)-4-R$^1$-cyclohexanols which can be dehydrated to give 1-(4-R$^2$-Cy)-4-R$^1$-cyclohexenes.

The reduction can be effected, for example, by catalytic hydrogenation at temperatures between about 0° and about 200° and under pressures between about 1 and 200 bar in an inert solvent, for example an alcohol, such as methanol, ethanol or isopropanol, an ether, such as tetrahydrofuran (THF) or dioxane, an ester, such as ethyl acetate, a carboxylic acid, such as acetic acid, or a hydrocarbon, such as cyclohexane. Suitable catalysts are preferably noble metals, such as Pt or Pd, which can be employed in the form of oxides (for example PtO$_2$ or PdO) on a support (for example Pd on charcoal, calcium carbonate or strontium carbonate) or in a finely divided form.

Ketones can also be reduced by the methods of Clemmensen (using zinc, amalgamated zinc or tin and hydrochloric acid, preferably in an aqueous-alcoholic solution or in a heterogeneous phase containing water/toluene at temperatures between about 80° and 120°) or Wolff-Kishner (using hydrazine, preferably in the presence of an alkali, such as KOH or NaOH, in a high-boiling solvent, such as diethylene glycol or triethylene glycol, at temperatures between about 100° and 200°) to give the corresponding compounds of the formula I containing a CH$_2$ group instead of the keto group.

Reduction by means of complex hydrides is also possible. For example, arylsulfonyloxy groups can be removed reductively using LiAlH$_4$, in particular p-toluenesulfonyloxymethyl groups can be reduced to give methyl groups, preferably in an inert solvent, such as diethyl ether or THF, at temperatures between about 0° and 100°. Double bonds can be hydrogenated by means of NaBH$_4$ or tributyltin hydride in methanol.

Ethers of the formula I (wherein at least one of the radicals R$^1$ and R$^2$ is an alkyl group wherein one or two CH$_2$ group(s) have been replaced by O atoms) can be obtained by etherifying corresponding hydroxy compounds.

Corresponding hydroxy compounds are either known or can be prepared in a manner which is in itself known. Thus, for example, bicyclohexyl-4-ols of the type R$^1$—Cy—Cy—OH can be obtained by reducing corresponding ketones, and carbinols of the type R$^1$—Cy—Cy—(CH$_2$)$_n$—OH wherein n is an integer between 1 and 9 can be obtained by reducing corresponding carboxylic acids.

For the etherification reaction, the hydroxy compound can first be converted into a corresponding metal derivative, for example can be converted by treatment with Na, K, NaH or KH into the corresponding alkali metal alcoholate. The latter can then be reacted with an alkyl halide or sulfonate or a dialkyl sulfate, preferably in the presence of an inert solvent, such as acetone, 1,2-dimethoxyethane, THF, dimethylformamide or dimethyl sulfoxide, at temperatures between about 20° and 100°.

The dielectrics according to the invention comprise 2 to 15, preferably 3 to 12, components, including at least one compound of the formula I. The other constituents are preferably selected from the nematic or nematogenic substances (in particular the known substances) belonging to the classes comprising azoxybenzenes, benzylideneanilines, biphenyls, terphenyls, phenyl or cyclohexyl benzoates, phenyl or cyclohexyl cyclohexanecarboxylates, phenylcyclohexanes, cyclohexylbiphenyls, cyclohexylcyclohexane, cyclohexylnaphthalenes, 1,4-bis-cyclohexylbenzenes, 4,4'-bis-cyclohexylbiphenyls, phenylpyrimidines, cyclohexylpyrimidines, phenyldioxanes, cyclohexyldioxanes, optionally halogenated stilbenes, benzyl phenyl ethers, tolanes, substituted cinnamic acids, naphthalenes, dihydronaphthalenes, tetrahydronaphthalenes and decahydronaphthalenes.

The most important compounds which are suitable as constituents of liquid-crystal dielectrics of this type can be characterized by the formula II

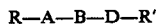

R—A—B—D—R'  II wherein A and D are each a carbocyclic or heterocyclic ring system composed of groups formed from 1,4-disubstituted benzene and cyclohexane rings, 4,4'-disubstituted biphenyl, phenylcyclohexane and cyclohexylcyclohexane systems, 2,5-disubstituted pyrimidine and 1,3-dioxane rings, 2,6-disubstituted naphthalene, dihydronaphthalene, tetrahydronaphthalene and decahydronaphthalene, quinazoline and tetrahydroquinazoline, B is

| —CH=CH— | —N(O)=N— |
| —CH=CY— | —CH=N(O)— |
| —C≡C— | —CH$_2$—CH$_2$— |
| —CO—O— | —CH$_2$—O— |
| —CO—S— | —CH$_2$—S— |
| —CH=N— | —COO—Ph—COO— | or a C—C single bond, Y is halogen, preferably chlorine, or —CN, and R and R' are alkyl, alkoxy, alkanoytoxy or alkoxycarbonyloxy having up to 18, preferably up to 8, carbon atoms, or one of these radicals is also —CN, —NC, —NO$_2$, —CF$_3$, F, Cl or Br.

In most of these compounds R and R' are different from one another, and one of these radicals is in most cases an alkyl or alkoxy group. However, other variants of the scheduled substituents are also customary. Many of such substances or mixtures fthereof are commercially available.

The preparation of the dielectrics according to the invention is effected in a manner which is in itself customary. As a rule, the components are dissolved in one another, preferably at an elevated temperature.

The liquid-crystal dielectrics according to the invention can be modified by means of suitable additives in such a way that they can be used in all types of liquid-crystal display elements hitherto disclosed.

Additives of this type are known to those skilled in the art and are described in detail in the literature. For example it is possible to add conductivity salts, preferably ethyldimethyldodecylammonium 4-hexyloxybenzoate, tetrabutylammonium tetraphenylboranate or complex salts of crown ethers (cf., for example, I. Haller et al., Mol. Cryst. Liq. Cryst. Volume 24, pages 249-258 (1973)) for improving conductivity, dichroic dyestuffs or substances for modifying the dielectric anisotropy, the viscosity and/or the orientation of the nematic phases. Substances of this type are described, for example, in German Offenlegungsschriften 2,209,127, 2,240,864, 2,321,632, 2,338,281, 2,450,088, 2,637,430, 2,853,728 and 2,902,177.

One skilled in the art can, using the preceding description, utilize the present invention to its fullest extent. The following preferred specific embodiments are, therefore, to be construed as merely illustrative, and not limitative of the remainder of the disclosure in any way whatsoever. In the following examples and in the preceding text, all temperatures are set forth uncorrected in degrees Celsius and all parts and percentages are by weight, unless otherwise indicated.

In the examples, m.p. is the melting point and c.p. is the clear point of a liquid crystal substance.

"Customary working up" means the following: water is added, the mixture is extracted with methylene dichloride or toluene, the phases are separated, the organic phase is dried with sodium sulfate and evaporated, and the product is purified by distillation, crystallization and/or chromatography.

EXAMPLE 1

A mixture of 26.4 g of trans,trans-4-propionyl-4'-propylbicyclohexyl (obtainable by reacting trans,trans-4-cyano-4'-propylbicyclohexyl with C$_2$H$_5$MgBr, and hydrolysing the product), 30 g of KOH, 50 ml of 85% hydrazine and 500 ml of triethylene glycol is heated at 120° for 1 hour. The temperature is raised slowly until the decomposition of the resulting hydrazone is achieved, and the mixture is boiled for a further 4 hours, cooled and worked up in the customary manner to give trans,trans-4,4'-dipropylbicyclohexyl, c.p. 41°.

The following are obtained analogously by Wolff-Kishner reduction of the corresponding ketones:
trans,trans-4,4'-Diethylbicyclohexyl
trans,trans-4-Ethyl-4'-propylbicyclohexyl
trans,trans-4-Ethyl-4'-butylbicyclohexyl
trans,trans-4-Ethyl-4'-pentylbicyclohexyl
trans,trans-4-Ethyl-4'-hexylbicyclohexyl
trans,trans-4-Ethyl-4'-heptylbicyclohexyl
trans,trans-4-Ethyl-4'-octylbicyclohexyl
trans,trans-4-Ethyl-4'-nonylbicyclohexyl
trans,trans-4-Ethyl-4'-decylbicyclohexyl
trans,trans-4-Propyl-4'-butylbicyclohexyl
trans,trans-4-Propyl-4'-pentylbicyclohexyl
trans,trans-4-Propyl-4'-hexylbicyclohexyl
trans,trans-4-Propyl-4'-heptylbicyclohexyl
trans,trans-4-Propyl-4'-octylbicyclohexyl
trans,trans-4-Propyl-4'-nonylbicyclohexyl
trans,trans-4-Propyl-4'-decylbicyclohexyl
trans,trans-4,4'-Dibutylbicyclohexyl
trans,trans-4-Butyl-4'-pentylbicyclohexyl
trans,trans-4-Butyl-4'-hexylbicyclohexyl
trans,trans-4-Butyl-4'-heptylbicyclohexyl
trans,trans-4-Butyl-4'-octylbicyclohexyl
trans,trans-4-Butyl-4'-nonylbicyclohexyl
trans,trans-4-Butyl-4'-decylbicyclohexyl
trans,trans-4,4'-Dipentylbicyclohexyl
trans,trans-4-Pentyl-4'-hexylbicyclohexyl
trans,trans-4-Pentyl-4'-heptylbicyclohexyl
trans,trans-4-Pentyl-4'-octylbicyclohexyl
trans,trans-4-Pentyl-4'-nonylbicyclohexyl
trans,trans-4-Pentyl-4'-decylbicyclohexyl
trans,trans-4,4'-Dihexylbicyclohexyl
trans,trans-4-Hexyl-4'-heptylbicyclohexyl
trans,trans-4-Hexyl-4'-octylbicyclohexyl
trans,trans-4-Hexyl-4'-nonylbicyclohexyl
trans,trans-4-Hexyl-4'-decylbicyclohexyl
trans,trans-4,4'-Diheptylbicyclohexyl
trans,trans-4-Heptyl-4'-octylbicyclohexyl
trans,trans-4-Heptyl-4'-nonylbicyclohexyl
trans,trans-4-heptyl-4'-decylbicyclohexyl
trans,trans-4,4'-Dioctylbicyclohexyl
trans,trans-4-Octyl-4'-nonylbicyclohexyl
trans,trans-4-Octyl-4'-decylbicyclohexyl
trans,trans-4,4'-Dinonylbicyclohexyl
trans,trans-4-Nonyl-4'-decylbicyclohexyl
trans,trans-4,4'-Didecylbicyclohexyl.

EXAMPLE 2

A solution in 250 ml of THF of 42 g of trans,trans-4-p-tolylsulfonyloxymethyl-4'-pentylbicyclohexyl (obtainable by hydrolysis of trans,trans-4-cyano-4'-pentylbicyclohexyl to give the carboxylic acid, LiAlH$_4$ reduction to give the carbinol and tosylation of the latter) is added dropwise, with stirring, to a mixture of 5 g of LiAlH$_4$ and 120 ml of THF, and stirring is continued for a further 12 hours at 68°. Cooling, evaporation and customary working up gives trans,trans-4-methyl-4'-pentylbicyclohexyl, c.p. 40.8°.

The following are obtained analogously from the corresponding tosylates:
trans,trans-4,4'-Dimethylbicyclohexyl
trans,trans-4-Methyl-4'-ethylbicyclohexyl
trans,trans-4-Methyl-4'-propylbicyclohexyl, m.p. 33°, c.p. 46°
trans,trans-4-Methyl-4'-butylbicyclohexyl
trans,trans-4-Methyl-4'-pentylbicyclohexyl
trans,trans-4-Methyl-4'-hexylbicyclohexyl
trans,trans-4-Methyl-4'-heptylbicyclohexyl
trans,trans-4-Methyl-4'-octylbicyclohexyl
trans,trans-4-Methyl-4'-nonylbicyclohexyl
trans,trans-4-Methyl-4'-decylbicyclohexyl

EXAMPLE 3

A solution of 24.4 g of trans-1-p-propylphenyl-4-propylcyclohexane in 500 ml of ethanol is hydrogenated over 1 g of PtO$_2$ for 1 hour at 60° and 100 bar, and the mixture is cooled, filtered and evaporated to give 4,4'-dipropylbicyclohexyl in the form of an oily mixture of isomers, which is taken up in 200 ml of boiling methanol. The resulting hot solution is poured into a boiling solution of 70 g of thiourea in 300 ml of methanol. The mixture is cooled to 0°, and the adduct which has been precipitated is filtered off and extracted by boiling with 300 ml of pertroleum ether (b.p. 40°-60°). The undissolved residue is heated with 350 ml of 2N aqueous potassium hydroxide solution for 30 minutes at 50°. The solution is acidified with $H_2SO_4$ to give, after customary working up, trans,trans-4,4'-dipropylbicyclohexyl, c.p. 41°.

Analogously, the hydrogenation of corresponding phenylcyclohexanes gives the following compounds in the form of mixtures of isomers from which the trans,-trans-isomers can be isolated via the thiourea compounds:
4,4'-Diethylbicyclohexyl
4-Ethyl-4'-propylbicyclohexyl, m.p. −6°, c.p. 67°
4-Ethyl-4'-butylbicyclohexyl
4-Ethyl-4'-pentylbicyclohexyl
4-Ethyl-4'-hexylbicyclohexyl
4-Ethyl-4'-heptylbicyclohexyl
4-Ethyl-4'-octylbicyclohexyl
4-Ethyl-4'-nonylbicyclohexyl
4-Ethyl-4'-decylbicyclohexyl.

EXAMPLE 4

A solution in 300 ml of cyclohexane of 24.8 g of 1-(trans-4-propylcyclohexyl)-4-propylcyclohexene [obtainable by reacting 4-propylcyclohexanone with 4-propylcyclohexylmagnesium bromide to give 1-(trans-4-propylcyclohexyl)-4-propylcyclohexanol and dehydrating the latter] is hydrogenated over 4 g of 10% PdC at 20° and 1 bar until absorption of $H_2$ ceases. The mixture is filtered and worked up analogously to Example 3 via the thiourea adduct to give trans,trans-4,4'-dipropylbicyclohexyl, c.p. 41°.

EXAMPLE 5

A solution of 22.4 g of trans,trans-4'-propylbicyclohexyl-4-ol in 200 ml of THF is added dropwise, at 50° and with stirring, to a mixture of 22 g of n-butyl iodide and 4.8 g of NaH in 250 ml of THF, and stirring is continued for a further 2 hours at 50°. Customary working up gives trans,trans-4-butoxy-4'-propylbicyclohexyl, c.p. 66°.

The following are obtained analogously from the corresponding alcohols by means of the corresponding alkyl bromides, iodides, chlorides or tosylates or alkoxyalkyl bromides, iodides, chlorides or tosylates, respectively:
trans,trans-4-Methoxy-4'-methylbicyclohexyl
trans,trans-4-Methoxy-4'-ethylbicyclohexyl
trans,trans-4-Methoxy-4'-propylbicyclohexyl, m.p. 9°, c.p. 15°
trans,trans-4-Methoxy-4'-butylbicyclohexyl, m.p. 7°, c.p. 27°
trans,trans-4-Methoxy-4'-pentylbicyclohexyl, m.p. 12°, c.p. 36°
trans,trans-4-Methoxy-4'-hexylbicyclohexyl
trans,trans-4-Methoxy-4'-heptylbicyclohexyl
trans,trans-4-Methoxy-4'-octylbicyclohexyl
trans,trans-4-Methoxy-4'-nonylbicyclohexyl
trans,trans-4-Methoxy-4'-decylbicyclohexyl
trans,trans-4,4'-Diethoxy-bicyclohexyl, m.p. 55°
trans,trans-4-(3-oxa-butyl)-4'-pentylbicyclohexyl, c.p. 74°
trans,trans-4-(1,4-dioxa-pentyl)-4'-propyl-bicyclohexyl, m.p. 44°, c.p. 38°
trans,trans-4-Ethoxy-4'-methylbicyclohexyl
trans,trans-4-Ethoxy-4'-ethylbicyclohexyl
trans,trans-4-Ethoxy-4'-propylbicyclohexyl, m.p. 45° C., c.p.
trans,trans-4-Ethoxy-4'-butylbicyclohexyl, m.p. 8°, c.p. 51°
trans,trans-4-Ethoxy-4'-pentylbicyclohexyl, m.p. 35°, c.p. 62°
trans,trans-4-Ethoxy-4'-hexylbicyclohexyl
trans,trans-4-Ethoxy-4'-heptylbicyclohexyl
trans,trans-4-Ethoxy-4'-octylbicyclohexyl
trans,trans-4-Ethoxy-4'-nonylbicyclohexyl
trans,trans-4-Ethoxy-4'-decylbicyclohexyl
trans,trans-4-Propoxy-4'-methylbicyclohexyl
trans,trans-4-Propoxy-4'-ethylbicyclohexyl
trans,trans-4-Propoxy-4'-propylbicyclohexyl, m.p. 14°, c.p. 64°
trans,trans-4-Propoxy-4'-butylbicyclohexyl, m.p. 7°, c.p. 78°
trans,trans-4-Propoxy-4'-pentylbicyclohexyl, m.p. 20°, c.p. 82°
trans,trans-4-Propoxy-4'-hexylbicyclohexyl
trans,trans-4-Propoxy-4'-heptylbicyclohexyl
trans,trans-4-Propoxy-4'-octylbicyclohexyl
trans,trans-4-Propoxy-4'-nonylbicyclohexyl
trans,trans-4-Propoxy-4'-decylbicyclohexyl
trans,trans-4-Butoxy-4'-methylbicyclohexyl
trans,trans-4-Butoxy-4'-ethylbicyclohexyl
trans,trans-4-Butoxy-4'-butylbicyclohexyl
trans,trans-4-Butoxy-4'-pentylbicyclohexyl
trans,trans-4-Butoxy-4'-hexylbicyclohexyl
trans,trans-4-Butoxy-4'-heptylbicyclohexyl
trans,trans-4-Butoxy-4'-octylbicyclohexyl
trans,trans-4-Butoxy-4'-nonylbicyclohexyl
trans,trans-4-Butoxy-4'-decylbicyclohexyl
trans,trans-4-Pentoxy-4'-methylbicyclohexyl
trans,trans-4-Pentoxy-4'-ethylbicyclohexyl
trans,trans-4-Pentoxy-4'-propylbicyclohexyl
trans,trans-4-Pentoxy-4'-butylbicyclohexyl
trans,trans-4-Pentoxy-4'-pentylbicyclohexyl
trans,trans-4-Pentoxy-4'-hexylbicyclohexyl
trans,trans-4-Pentoxy-4'-heptylbicyclohexyl
trans,trans-4-Pentoxy-4'-octylbicyclohexyl
trans,trans-4-Pentoxy-4'-nonylbicyclohexyl
trans,trans-4-Pentoxy-4'-decylbicyclohexyl
trans,trans-4-Hexoxy-4'-methylbicyclohexyl
trans,trans-4-Hexoxy-4'-ethylbicyclohexyl
trans,trans-4-hexoxy-4'-propylbicyclohexyl
trans,trans-4-Hexoxy-4'-butylbicyclohexyl
trans,trans-4-Hexoxy-4'-pentylbicyclohexyl
trans,trans-4-Hexoxy-4'-hexylbicyclohexyl
trans,trans-4-Hexoxy-4'-heptylbicyclohexyl
trans,trans-4-Hexoxy-4'-octylbicyclohexyl
trans,trans-4-Hexoxy-4'-nonylbicyclohexyl
trans,trans-4-Hexoxy-4'-decylbicyclohexyl
trans,trans-4-Heptoxy-4'-methylbicyclohexyl
trans,trans-4-Heptoxy-4'-ethylbicyclohexyl
trans,trans-4-Heptoxy-4'-propylbicyclohexyl
trans,trans-4-Heptoxy-4'-butylbicyclohexyl
trans,trans-4-Heptoxy-4'-pentylbicyclohexyl
trans,trans-4-Heptoxy-4'-hexylbicyclohexyl
trans,trans-4-Heptoxy-4'-heptylbicyclohexyl
trans,trans-4-Heptoxy-4'-octylbicyclohexyl
trans,trans-4-Heptoxy-4'-nonylbicyclohexyl trans,trans-4-Heptoxy-4'-decylbicyclohexyl
trans,trans-4-Octoxy-4'-methylbicyclohexyl
trans,trans-4-Octoxy-4'-ethylbicyclohexyl
trans,trans-4-Octoxy-4'-propylbicyclohexyl
trans,trans-4-Octoxy-4'-butylbicyclohexyl
trans,trans-4-Octoxy-4'-pentylbicyclohexyl
trans,trans-4-Octoxy-4'-hexylbicyclohexyl
trans,trans-4-Octoxy-4'-heptylbicyclohexyl
trans,trans-4-Octoxy-4'-octylbicyclohexyl
trans,trans-4-Octoxy-4'-nonylbicyclohexyl
trans,trans-4-Octoxy-4'-decylbicyclohexyl
trans,trans-4-Nonoxy-4'-methylbicyclohexyl
trans,trans-4-Nonoxy-4'-ethylbicyclohexyl
trans,trans-4-Nonoxy-4'-propylbicyclohexyl
trans,trans-4-Nonoxy-4'-butylbicyclohexyl
trans,trans-4-Nonoxy-4'-pentylbicyclohexyl
trans,trans-4-Nonoxy-4'-hexylbicyclohexyl
trans,trans-4-Nonoxy-4'-heptylbicyclohexyl
trans,trans-4-Nonoxy-4'-octylbicyclohexyl
trans,trans-4-Nonoxy-4'-nonylbicyclohexyl
trans,trans-4-Nonoxy-4'-decylbicyclohexyl
trans,trans-4-Decoxy-4'-methylbicyclohexyl
trans,trans-4-Decoxy-4'-ethylbicyclohexyl
trans,trans-4-Decoxy-4'-propylbicyclohexyl
trans,trans-4-Decoxy-4'-butylbicyclohexyl
trans,trans-4-Decoxy-4'-pentylbicyclohexyl
trans,trans-4-Decoxy-4'-hexylbicyclohexyl
trans,trans-4-Decoxy-4'-heptylbicyclohexyl
trans,trans-4-Decoxy-4'-octylbicyclohexyl
trans,trans-4-Decoxy-4'-nonylbicyclohexyl
trans,trans-4-Decoxy-4'-decylbicyclohexyl
trns,trans-4-Methoxymethyl-4'-methylbicyclohexyl
trans,trans-4-Methoxymethyl-4'-ethylbicyclohexyl
trans,trans-4-Methoxymethyl-4'-propylbicyclohexyl
trans,trans-4-Methoxymethyl-4'-butylbicyclohexyl
trans,trans-4-Methoxymethyl-4'-pentylbicyclohexyl
trans,trans-4-Methoxymethyl-4'-hexylbicyclohexyl
trans,trans-4-Methoxymethyl-4'-heptylbicyclohexyl
trans,trans-4-Methoxymethyl-4'-octylbicyclohexyl
trans,trans-4-Methoxymethyl-4'-nonylbicyclohexyl
trans,trans-4-Methoxymethyl-4'-decylbicyclohexyl
trans,trans-4-Ethoxymethyl-4'-methylbicyclohexyl
trans,trans-4-Ethoxymethyl-4'-ethylbicyclohexyl
trans,trans-4-Ethoxymethyl-4'-propylbicyclohexyl
trans,trans-4-Ethoxymethyl-4'-butylbicyclohexyl
trans,trans-4-Ethoxymethyl-4'-pentylbicyclohexyl
trans,trans-4-Ethoxymethyl-4'-hexylbicyclohexyl
trans,trans-4-Ethoxymethyl-4'-heptylbicyclohexyl
trans,trans-4-Ethoxymethyl-4'-octylbicyclohexyl
trans,trans-4-Ethoxymethyl-4'-nonylbicyclohexyl
trans,trans-4-Ethoxymethyl-4'-decylbicyclohexyl.

Examples of dielectrics according to the invention containing at least one compound of the formula I are given below:

EXAMPLE A

A mixture composed of:
16% of trans,trans-4-ethoxy-4'-propylbicyclohexyl,
12% of trans,trans-4-butoxy-4'-propylbicyclohexyl,
17% of p-trans-4-propylcyclohexylbenzonitrile,
23% of p-trans-4-pentylcyclohexylbenzonitrile,
22% of 4-ethyl-4'-(trans-4-pentylcyclohexyl)-biphenyl and
10% of 4-(trans-4-pentylcyclohexyl)-4'-(trans-4-propylcyclohexyl)-biphenyl has c.p. 87°.

EXAMPLE B

A mixture composed of:
16% of trans,trans-4,4'-dipropylbicyclohexyl,
15% of p-trans-4-propylcyclohexylbenzonitrile,
11% of p-trans-4-butylcyclohexylbenzonitrile,
21% of p-trans-4-pentylcyclohexylbenzonitrile,
4% of 4-cyano-4'-(trans-4-pentylcyclohexyl)-biphenyl,
21% of 4-ethyl-4'-(trans-4-pentylcyclohexyl)-biphenyl and
12% of 4-(trans-4-pentylcyclohexyl)-4'-(trans-4-propylcyclohexyl)-biphenyl has c.p. 88°.

The proceding examples can be repeated with similar succession by substituting the generically or specifically described reactants and/or operating conditions of this invention for those used in the proceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A bicyclohexyl of the formula $$R^1-Cy-Cy-R^2$$

wherein $R^1$ is alkyl or alkoxy each of which has up to 10 C atoms, $R^2$ is alkoxy of 1–10 C atoms, and Cy is 1,4-cyclohexylene.

2. A compound of claim 1 wherein $R^1$ is alkyl.

3. A compound of claim 1 wherein $R^1$ and $R^2$ are straight-chained.

4. A compound of claim 1 wherein $R^1$ and $R^2$ each contains 2–8 C atoms.

5. A compound of claim 1 wherein $R^1$ and $R^2$ are alkoxy.

6. A compound of claim 1, wherein $R^2$ is ethoxy, propoxy, butoxy, pentoxy, hexoxy, heptoxy or octoxy.

7. A compound of claim 6, wherein $R^2$ is butoxy.

8. A compound of claim 1, wherein $R^1$ is propyl, butyl, pentyl, hexyl, heptyl or octyl.

9. A compound according to claim 7, wherein $R^1$ is propyl.

* * * * *